(12) United States Patent
McCusker-Orth et al.

(10) Patent No.: US 7,521,583 B2
(45) Date of Patent: Apr. 21, 2009

(54) PROCESS FOR THE PREPARATION OF TETRAALKYLCYCLOBUTANE-1,3-DIOL IN THE PRESENCE OF A COBALT-BASED CATALYST

(75) Inventors: Jennifer Ellen McCusker-Orth, Kingsport, TN (US); Jerome Leonard Stavinoha, Jr., Longview, TX (US); Anthony Dominick Messina, Kingsport, TN (US); Steven Thomas Perri, Kingsport, TN (US); Zhufang Liu, Kingsport, TN (US); Philip Conrad Heidt, Kingsport, TN (US); Brent Alan Tennant, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 11/948,047

(22) Filed: Nov. 30, 2007

(65) Prior Publication Data

US 2008/0132739 A1    Jun. 5, 2008

Related U.S. Application Data

(60) Provisional application No. 60/872,470, filed on Dec. 2, 2006.

(51) Int. Cl.
*C07C 35/04* (2006.01)
(52) U.S. Cl. .................. 568/839; 568/338; 568/301
(58) Field of Classification Search ................ 568/839, 568/338, 301
See application file for complete search history.

(56) References Cited

U.S. PATENT DOCUMENTS

| | | | |
|---|---|---|---|
| 1,602,699 A | 10/1926 | Nightingale | |
| 2,160,841 A | 6/1939 | Dreyfus | |
| 2,202,046 A | 5/1940 | Dreyfus et al. | |
| 2,278,537 A | 4/1942 | Dreyfus et al. | |
| 2,806,064 A | 9/1957 | Mcklveen | |
| 2,936,324 A | 5/1960 | Hasek et al. | |
| 3,000,906 A | 9/1961 | Hasek et al. | |
| 3,190,928 A | 6/1965 | Elam et al. | |
| 3,201,474 A | 8/1965 | Hasek et al. | |
| 3,227,764 A | 1/1966 | Martin et al. | |
| 3,236,899 A | 2/1966 | Clark et al. | |
| 3,259,469 A | 7/1966 | Painter et al. | |
| 3,287,390 A | 11/1966 | Poos et al. | |
| 3,288,854 A | 11/1966 | Martin et al. | |
| 3,312,741 A | 4/1967 | Martin et al. | |
| 3,329,722 A | 7/1967 | Rylander | |
| 3,366,689 A | 1/1968 | Maeda et al. | |
| 3,403,181 A | 9/1968 | Painter et al. | |
| 5,118,847 A | 6/1992 | Jackson et al. | |
| 5,169,994 A * | 12/1992 | Sumner, Jr. et al. | 568/839 |
| 5,258,556 A * | 11/1993 | Sumner, Jr. et al. | 568/839 |
| 5,475,144 A | 12/1995 | Watson et al. | |
| 6,232,504 B1 | 5/2001 | Barteau et al. | |

OTHER PUBLICATIONS

USPTO Office Action dated Apr. 1, 2008 for co-pending U.S. Appl. No. 11/948,000.
USPTO Office Action dated Jun. 25, 2008 for co-pending U.S. Appl. No. 11/947,981.
USPTO Notice of Allowance dated Jul. 3, 2008 for co-pending U.S. Appl. No. 11/947,941.
Co-Pending U.S. Appl. No. 11/948,000, filed Nov. 30, 2007, Jennifer Ellen Mccusker-Orth, et al.
Co-Pending U.S. Appl. No. 11/947,981, filed Nov. 30, 2007, Jennifer Ellen Mccusker-Orth, et al.
Co-Pending U.S. Appl. No. 11/948,032, filed Nov. 30, 2007, Jennifer Ellen Mccusker-Orth, et al.
Co-Pending U.S. Appl. No. 11/947,941, filed Nov. 30, 2007, Jennifer Ellen Mccusker-Orth, et al.
Co-Pending U.S. Appl. No. 11/947,950, filed Nov. 30, 2007, Jennifer Ellen Mccusker-Orth, et al.

* cited by examiner

*Primary Examiner*—Elvis O Price
(74) *Attorney, Agent, or Firm*—Louis N. Moreno; Bernard J. Graves, Jr.

(57) ABSTRACT

The present invention relates to the production of 2,2,4,4-tetramethylcyclobutane-1,3-diol. In one embodiment, the present invention relates to the production of 2,2,4,4-tetramethylcyclobutane-1,3-diol by hydrogenation of 2,2,4,4-tetramethylcyclobutane-1,3-dione in the presence of a cobalt-based catalyst.

22 Claims, No Drawings

PROCESS FOR THE PREPARATION OF TETRAALKYLCYCLOBUTANE-1,3-DIOL IN THE PRESENCE OF A COBALT-BASED CATALYST

CROSS REFERENCES TO RELATED APPLICATIONS

This application claims priority under 35 U.S.C. § 119(e) to U.S. Provisional Application Ser. No. 60/872,470 filed on Dec. 2, 2006, which is hereby incorporated by reference.

FIELD OF THE INVENTION

The present invention relates to the production of 2,2,4,4-tetramethylcyclobutane-1,3-diol. In one embodiment, the present invention relates to the production of 2,2,4,4-tetramethylcyclobutane-1,3-diol by hydrogenation of 2,2,4,4-tetramethylcyclobutane-1,3-dione in the presence of a cobalt-based catalyst.

BACKGROUND OF THE INVENTION 2,2,4,4-Tetramethylcyclobutane-1,3-diol is an important intermediate for producing a variety of polymeric materials having advantageous properties. For example, polyesters derived from dicarboxylic acids and 2,2,4,4-tetramethylcyclobutane-1,3-diol possess higher glass transition temperatures, superior weatherability, and improved hydrolytic stability compared to polyesters prepared from other commonly-used, polyester forming diols. A 2,2,4,4-tetramethylcyclobutane-1,3-diol of Formula I is typically produced by the catalytic hydrogenation of the corresponding 2,2,4,4-tetramethylcyclobutane-1,3-dione as shown below.

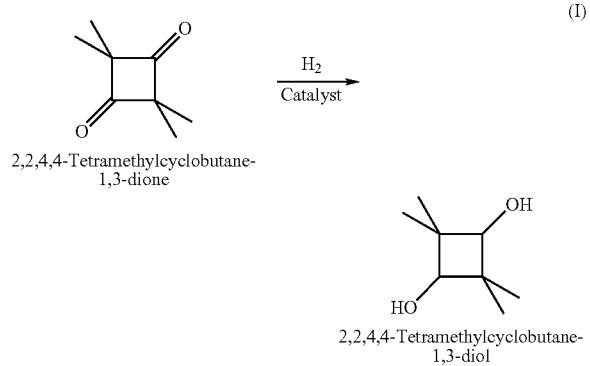

Typically, the hydrogenation of 2,2,4,4-tetramethylcyclobutane-1,3-dione produces the corresponding 2,2,4,4-tetramethylcyclobutane-1,3-diol as a mixture of cis and trans isomers. It would be desirable to produce 2,2,4,4-tetramethylcyclobutane-1,3-diol with a specific cis/trans isomer ratio in order to control glass transition temperatures and crystallization rates in copolyesters.

SUMMARY OF THE INVENTION

The present invention relates to the production of 2,2,4,4-tetramethylcyclobutane-1,3-diol. In one embodiment, the present invention relates to the production of 2,2,4,4-tetramethylcyclobutane-1,3-diol by hydrogenation of 2,2,4,4-tetramethylcyclobutane-1,3-dione in the presence of a cobalt-based catalyst.

In one embodiment, the present invention relates to a process for producing a 2,2,4,4-tetraalkylcyclobutane-1,3-diol, comprising contacting a 2,2,4,4-tetraalkylcyclobutane-1,3-dione with hydrogen in the presence of a cobalt-based catalyst under conditions of temperature and pressure sufficient to form a 2,2,4,4-tetraalkylcyclobutane-1,3-diol, wherein the alkyl radicals each independently have 1 to 8 carbon atoms.

In one embodiment, the present invention relates to a process for producing 2,2,4,4-tetramethylcyclobutane-1,3-diol, comprising contacting 2,2,4,4-tetramethylcyclobutane-1,3-dione, a cobalt-based catalyst, a non-protic solvent, and hydrogen in a hydrogenation zone under conditions of temperature and pressure sufficient to form 2,2,4,4-tetramethylcyclobutane-1,3-diol.

In one embodiment, the present invention relates to a process comprising: (1) feeding isobutyric anhydride to a pyrolysis zone, wherein the isobutyric anhydride is heated at a temperature of 350° C. to 600° C. to produce a vapor effluent comprising dimethylketene, isobutyric acid, and unreacted isobutyric anhydride; (2) cooling the vapor effluent to condense isobutyric acid and isobutyric anhydride and separating the condensate from the dimethylketene vapor; (3) feeding the dimethylketene vapor to an absorption zone, wherein the dimethylketene vapor is contacted with and dissolved in a solvent comprising an ester containing 4 to 20 carbon atoms and consisting of residues of an aliphatic carboxylic acid and an alkanol to produce an effluent comprising a solution of dimethylketene in the solvent; (4) feeding the absorption zone effluent to a dimerization zone wherein the effluent is heated at a temperature ranging from 70° C. to 140° C. to convert dimethylketene to 2,2,4,4-tetramethylcyclobutane-1,3-dione to produce an effluent comprising a solution of 2,2,4,4-tetramethylcyclobutane-1,3-dione in the solvent; and (5) contacting the 2,2,4,4-tetramethylcyclobutane-1,3-dione with hydrogen in the presence of a cobalt-based catalyst under conditions of temperature and pressure sufficient to form a 2,2,4,4-tetramethylcyclobutane-1,3-diol.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

DETAILED DESCRIPTION OF THE INVENTION

The present invention may be understood more readily by reference to the following detailed description of certain embodiments of the invention and the working examples.

In accordance with the purpose of this invention, certain embodiments of the invention are described in the Summary of the Invention and are further described herein below. Also, other embodiments of the invention are described herein.

The term "cobalt-based catalyst" refers to a cobalt-based catalyst that consists essentially of cobalt as the catalytic metal, but which may also comprise a binder and/or support. The cobalt-based catalyst may further comprise a binder and/or support.

The term cobalt-based catalyst refers to a catalyst consisting essentially of cobalt including, for example and without limitation, zero valent cobalt, cobalt in an ionic form, and cobalt in an alloy.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example, 1, 2, 3, 4, etc., as well as all fractional numbers between 0 and 10, for example, 1.5, 2.3, 4.57, 6.1113, etc., and the endpoints 0 and 10. Also, a range associated with chemical substituent groups such as, for example, "$C_1$ to $C_5$ hydrocarbons," is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the appended claims, the singular forms "a," "an," and "the" include their plural referents unless the context clearly dictates otherwise. For example, reference to the processing or making of a "catalyst," or a "promoter," is intended to include the processing or making of a plurality of catalysts, or promoters. References to a composition containing or including "an" alkyl radical or "a" catalyst is intended to include other alkyl radicals or other catalysts, respectively, in addition to the one named.

By "comprising" or "containing" or "including" we mean that at least the named compound, element, particle, or method step, etc., is present in the composition or article or method, but we do not exclude the presence of other compounds, catalysts, materials, particles, method steps, etc., even if the other such compounds, materials, particles, method steps, etc., have the same function as what is named, unless expressly excluded in the claims.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and the recited lettering can be arranged in any sequence, unless otherwise indicated.

In one embodiment, the present invention provides processes for making a 2,2,4,4-tetraalkylcyclobutane-1,3-diol by hydrogenation of a 2,2,4,4-tetraalkylcyclobutane-1,3-dione. In a general embodiment, the invention provides processes for making a 2,2,4,4-tetraalkylcyclobutane-1,3-diol comprising contacting a 2,2,4,4-tetraalkylcyclobutane-1,3-dione with hydrogen in the presence of a cobalt-based catalyst. In one embodiment, the present invention is useful for the preparation of 2,2,4,4-tetramethylcyclobutane-1,3-diol from 2,2,4,4-tetramethylcyclobutane-1,3-dione.

The hydrogenation reaction of 2,2,4,4-tetraalkylcyclobutane-1,3-dione to produce a 2,2,4,4-tetraalkylcyclobutane-1,3-diol of Formula II is shown below:

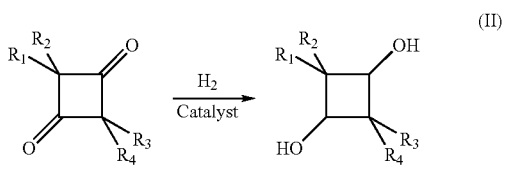

wherein $R_1$, $R_2$, $R_3$, and $R_4$ each independently represent an alkyl radical, for example, a lower alkyl radical having 1 to 8 carbon atoms. The alkyl radicals may be linear, branched, or a combination of linear and branched alkyl radicals. The 2,2,4,4-tetraalkylcyclobutane-1,3-dione, for example, 2,2,4,4-tetramethylcyclobutane-1,3-dione, is hydrogenated to the corresponding 2,2,4,4-tetraalkylcyclobutane-1,3-diol, for example, 2,2,4,4-tetramethylcyclobutane-1,3-diol, in accordance with the present processes.

In one embodiment, the alkyl radicals $R_1$, $R_2$, $R_3$, and $R_4$ on the 2,2,4,4-tetraalkylcyclobutane-1,3-dione each independently have 1 to 8 carbon atoms. Other 2,2,4,4-tetraalkylcyclobutane-1,3-diones that are suitably reduced to the corresponding diols include, but are not limited to, 2,2,4,4-tetraethylcyclobutane-1,3-dione, 2,2,4,4-tetra-n-propylcyclobutane-1,3-dione, 2,2,4,4-tetra-n-butylcyclobutane-1,3-dione, 2,2,4,4-tetra-n-amylcyclobutane-1,3-dione, 2,2,4,4-tetra-n-hexylcyclobutane-1,3-dione, 2,2,4,4-tetra-n-heptylcyclobutane-1,3-dione, 2,2,4,4-tetra-n-octylcyclobutane-1,3-dione, 2,2-dimethyl-4,4-diethylcyclobutane-1,3-dione, 2-ethyl-2,4,4-trimethylcyclobutane-1,3-dione, 2,4-dimethyl-2,4-diethylcyclobutane-1,3-dione, 2,4-dimethyl-2,4-di-n-propylcyclobutane-1,3-dione, 2,4-n-dibutyl-2,4-diethylcyclobutane-1,3-dione, 2,4-dimethyl-2,4-diisobutylcyclobutane-1,3-dione, and 2,4-diethyl-2,4-diisoamylcyclobutane-1,3-dione.

In other embodiments, the alkyl radicals $R_1$, $R_2$, $R_3$, and $R_4$ on the 2,2,4,4-tetraalkylcyclobutane-1,3-dione each independently have 1 to 6 carbon atoms, or 1 to 5 carbon atoms, or 1 to 4 carbon atoms, or 1 to 3 carbon atoms, or 1 to 2 carbon atoms.

In another embodiment, the alkyl radicals $R_1$, $R_2$, $R_3$, and $R_4$ on the 2,2,4,4-tetraalkylcyclobutane-1,3-dione each have 1 carbon atom.

Suitable supports for the cobalt-based catalysts include, but are not limited to, silica, alumina, aluminosilicate, silica/alumina, kieselguhr, titania, graphite, silicon carbide, carbon, zirconia, chromate, barium chromate, zinc oxide, clay, and alumina-clay. Suitable forms of the support include powder, extrudate, spheres, or pellets. The cobalt ranges from 1 to 70 wt %, or 5 to 65 wt %, or 10 to 60 wt %, based on the total weight of the catalyst.

The hydrogenation processes typically are conducted at temperatures in the range of 75° C. to 250° C. The hydrogenation processes typically are conducted at pressures in the range of 689 kPa (100 psi) (7 bar) to 41,368 kPa (6000 psi) (420 bar). Further examples of temperatures and/or pressures at which the hydrogenation processes of the invention may be operated are 120° C. to 200° C. at 1,380 kPa (200 psi) (14 bar) to 20,684 kPa (3000 psi) (207 bar), and 130° C. to 180° C. at 2,068 kPa (300 psi) (21 bar) to 14,789 kPa (2000 psi) (140 bar). For certain embodiments of the present invention, the hydrogenation process has a temperature ranging from 130° C. to 140° C. and a pressure ranging from 3450 kPa (500 psi) (34.5 barg) to 10000 kPa (1450 psi) (100 barg). For certain embodiments of the present invention, the hydrogenation process has a temperature ranging from 160° C. to 170° C. and a pressure ranging from 3450 kPa (500 psi) (34.5 barg) to 10000 kPa (1450 psi) (100 barg). For certain embodiments, the hydrogenation process has a temperature ranging from 110° C. to 170° C. and a pressure ranging from 210 kPa (300 psig) to 13,800 kPa (2000 psig).

For certain embodiments of the present invention, the hydrogenation process has a temperature range chosen from 75° C. to 250° C., 80° C. to 250° C., 90° C., to 250° C., 100° C. to 250° C., 110° C. to 250° C., 120° C. to 250° C., 130° C. to 250° C., 140° C. to 250° C., 150° C. to 250° C., 160° C. to 250° C., 170° C. to 250° C., 180° C. to 250° C., 190° C. to 250° C., 200° C. to 250° C., 210° C. to 250° C., 220° C. to 250° C., 230° C. to 250° C., or 240° C. to 250° C. For certain embodiments of the present invention, the hydrogenation process has a temperature range chosen from 75° C. to 240° C., 80° C. to 240° C., 90° C. to 240° C., 100° C. to 240° C., 110° C. to 240° C., 120° C., to 240° C., 130° C. to 240° C., 140° C. to 240° C., 150° C. to 240° C., 160° C. to 240° C., 170° C. to 240° C., 180° C. to 240° C., 190° C. to 240° C., 200° C. to 240° C., 210° C. to 240° C., 220° C. to 240° C., or 230° C. to 240° C. For certain embodiments of the present invention, the hydrogenation process has a temperature range chosen from 75° C. to 230° C., 80° C. to 230° C., 90° C. to 230° C., 100° C. to 230° C., 110° C. to 230° C., 120° C., to 230° C., 130° C. to 230° C., 140° C. to 230° C., 150° C. to 230° C., 160° C. to 230° C., 170° C. to 230° C., 180° C. to 230° C., 190° C. to 230° C., 200° C. to 230° C., 210° C. to 230° C., or 220° C. to 230° C.

For certain embodiments of the present invention, the hydrogenation process has a temperature range chosen from 75° C. to 220° C., 80° C. to 220° C., 90° C., to 220° C., 100° C. to 220° C., 110° C. to 220° C., 120° C. to 220° C., 130° C. to 220° C., 140° C. to 220° C., 150° C. to 220° C., 160° C. to 220° C., 170° C. to 220° C., 180° C. to 220° C., 190° C. to 220° C., 200° C. to 220° C., or 210° C. to 220° C. For certain embodiments of the present invention, the hydrogenation process has a temperature range chosen from 75° C. to 210° C., 80° C. to 210° C., 90° C. to 210° C., 100° C. to 210° C., 110° C. to 210° C., 120° C. to 210° C., 130° C. to 210° C., 140° C. to 210° C., 150° C. to 210° C., 160° C. to 210° C., 170° C. to 210° C., 180° C. to 210° C., 190° C. to 210° C., or 200° C. to 210° C. For certain embodiments of the present invention, the hydrogenation process has a temperature range chosen from 75° C. to 200° C., 80° C. to 200° C., 90° C., to 200° C., 100° C. to 200° C., 110° C. to 200° C., 120° C. to 200° C., 130° C. to 200° C., 140° C. to 200° C., 150° C. to 200° C., 160° C. to 200° C., 170° C. to 200° C., 180° C. to 200° C., or 190° C. to 200° C.

For certain embodiments of the present invention, the hydrogenation process has a temperature range chosen from 75° C. to 190° C., 80° C. to 190° C., 90° C., to 190° C., 100° C. to 190° C., 110° C. to 190° C., 120° C. to 190° C., 130° C. to 190° C., 140° C. to 190° C., 150° C. to 190° C., 160° C. to 190° C., 170° C. to 190° C., or 180° C. to 190° C. For certain embodiments of the present invention, the hydrogenation process has a temperature range chosen from 75° C. to 180° C., 80° C. to 180° C., 90° C. to 180° C., 100° C. to 180° C., 110° C. to 180° C., 120° C. to 180° C., 130° C. to 180° C., 140° C. to 180° C., 150° C. to 180° C., 160° C. to 180° C., or 170° C. to 180° C. For certain embodiments of the present invention, the hydrogenation process has a temperature range chosen from 75° C. to 170° C., 80° C. to 170° C., 90° C. to 170° C., 100° C. to 170° C., 110° C. to 170° C., 120° C. to 170° C., 130° C. to 170° C., 140° C. to 170° C., 150° C. to 170° C., or 160° C. to 170° C.

For certain embodiments of the present invention, the hydrogenation process has a temperature range chosen from 75° C. to 160° C., 80° C. to 160° C., 90° C. to 160° C., 100° C. to 160° C., 110° C. to 160° C., 120° C. to 160° C., 130° C. to 160° C., 140° C. to 160° C., or 150° C. to 160° C. For certain embodiments of the present invention, the hydrogenation process has a temperature range chosen from 75° C. to 150° C., 80° C. to 150° C., 90° C. to 150° C., 100° C. to 150° C., 110° C. to 150° C., 120° C. to 150° C., 130° C. to 150° C., or 140° C. to 150° C. For certain embodiments of the present invention, the hydrogenation process has a temperature range chosen from 75° C. to 140° C., 80° C. to 140° C., 90° C. to 140° C., 100° C. to 140° C., 110° C. to 140° C., 120° C. to 140° C., or 130° C. to 140° C. For certain embodiments of the present invention, the hydrogenation process has a temperature range chosen from 75° C. to 130° C., 80° C. to 130° C., 90° C. to 130° C., 100° C. to 130° C., 110° C. to 130° C., or 120° C. to 130° C.

For certain embodiments of the present invention, the hydrogenation process has a temperature range chosen from 75° C. to 120° C., 80° C. to 120° C., 90° C. to 120° C., 100° C. to 120° C., or 110° C. to 120° C. For certain embodiments of the present invention, the hydrogenation process has a temperature range chosen from 75° C. to 110° C., 80° C. to 110° C., 90° C. to 110° C., or 100° C. to 110° C. For certain embodiments of the present invention, the hydrogenation process has a temperature range chosen from 75° C. to 100° C., 80° C. to 100° C., or 90° C. to 100° C. For certain embodiments of the present invention, the hydrogenation process has a temperature range chosen from 75° C. to 90° C., or 80° C. to 90° C. For certain embodiments of the present invention, the hydrogenation process has a temperature range chosen from 75° C. to 80° C.

For certain embodiments of the present invention, the hydrogenation process has a pressure range chosen from 100 psi to 6000 psi, 200 psi to 6000 psi, 300 psi to 6000 psi, 400 psi to 6000 psi, 500 psi to 6000 psi, 1000 psi to 6000 psi, 1500 psi to 6000 psi, 2000 psi to 6000 psi, 2500 psi to 6000 psi, 3000 psi to 6000 psi, 3500 psi to 6000 psi, 4000 psi to 6000 psi, 4500 psi to 6000 psi, 5000 psi to 6000 psi, or 5500 psi to 6000 psi. For certain embodiments of the present invention, the hydrogenation process has a pressure range chosen from 100 psi to 5500 psi, 200 psi to 5500 psi, 300 psi to 5500 psi, 400 psi to 5500 psi, 500 psi to 5500 psi, 1000 psi to 5500 psi, 1500 psi to 5500 psi, 2000 psi to 5500 psi, 2500 psi to 5500 psi, 3000 psi to 5500 psi, 3500 psi to 5500 psi, 4000 psi to 5500 psi, 4500 psi to 5500 psi, or 5000 psi to 5500 psi.

For certain embodiments of the present invention, the hydrogenation process has a pressure range chosen from 100 psi to 5000 psi, 200 psi to 5000 psi, 300 psi to 5000 psi, 400 psi to 5000 psi, 500 psi to 5000 psi, 1000 psi to 5000 psi, 1500 psi to 5000 psi, 2000 psi to 5000 psi, 2500 psi to 5000 psi, 3000 psi to 5000 psi, 3500 psi to 5000 psi, 4000 psi to 5000 psi, or 4500 psi to 5000 psi. For certain embodiments of the present invention, the hydrogenation process has a pressure range chosen from 100 psi to 4500 psi, 200 psi to 4500 psi, 300 psi to 4500 psi, 400 psi to 4500 psi, 500 psi to 4500 psi, 1000 psi to 4500 psi, 1500 psi to 4500 psi, 2000 psi to 4500 psi, 2500 psi to 4500 psi, 3000 psi to 4500 psi, 3500 psi to 4500 psi, or 4000 psi to 4500 psi. For certain embodiments of the present invention, the hydrogenation process has a pressure range chosen from 100 psi to 4000 psi, 200 psi to 4000 psi, 300 psi to 4000 psi, 400 psi to 4000 psi, 500 psi to 4000 psi, 1000 psi to 4000 psi, 1500 psi to 4000 psi, 2000 psi to 4000 psi, 2500 psi to 4000 psi, 3000 psi to 4000 psi, or 3500 psi to 4000 psi.

For certain embodiments of the present invention, the hydrogenation process has a pressure range chosen from 100 psi to 3500 psi, 200 psi to 3500 psi, 300 psi to 3500 psi, 400 psi to 3500 psi, 500 psi to 3500 psi, 1000 psi to 3500 psi, 1500 psi to 3500 psi, 2000 psi to 3500 psi, 2500 psi to 3500 psi, or 3000 psi to 3500 psi. For certain embodiments of the present invention, the hydrogenation process has a pressure range chosen from 100 psi to 3000 psi, 200 psi to 3000 psi, 300 psi to 3000 psi, 400 psi to 3000 psi, 500 psi to 3000 psi, 1000 psi to 3000 psi, 1500 psi to 3000 psi, 2000 psi to 3000 psi, or 2500 psi to 3000 psi. For certain embodiments of the present invention, the hydrogenation process has a pressure range chosen from 100 psi to 2500 psi, 200 psi to 2500 psi, 300 psi to 2500 psi, 400 psi to 2500 psi, 500 psi to 2500 psi, 1000 psi to 2500 psi, 1500 psi to 2500 psi, 2000 psi to 2500 psi.

For certain embodiments of the present invention, the hydrogenation process has a pressure range chosen from 100 psi to 2000 psi, 200 psi to 2000 psi, 300 psi to 2000 psi, 400 psi to 2000 psi, 500 psi to 2000 psi, 1000 psi to 2000 psi, or 1500 psi to 2000 psi. For certain embodiments of the present invention, the hydrogenation process has a pressure range chosen from 100 psi to 1500 200 psi to 1500 psi, 300 psi to 1500 psi, 400 psi to 1500 psi, 500 psi to 1500 psi, or 1000 psi to 1500 psi. For certain embodiments of the present invention, the hydrogenation process has a pressure range chosen from 100 psi to 1000 psi, 200 psi to 1000 psi, 300 psi to 1000 psi, 400 psi to 1000 psi, or 500 psi to 1000 psi.

For certain embodiments of the present invention, the hydrogenation process has a pressure range chosen from 100 psi to 500 psi, 200 psi to 500 psi, 300 psi to 500 psi, or 400 psi to 500 psi. For certain embodiments of the present invention, the hydrogenation process has a pressure range chosen from 100 psi to 400 psi, 200 psi to 400 psi, or 300 psi to 400 psi. For certain embodiments of the present invention, the hydrogenation process has a pressure range chosen from 100 psi to 300 psi, or 200 psi to 300 psi. For certain embodiments of the present invention, the hydrogenation process has a pressure range chosen from 100 psi to 200 psi.

It is contemplated that the processes of the invention can be carried out at at least one of the temperature ranges disclosed herein and at least one of the pressure ranges disclosed herein. In certain embodiments of the hydrogenation process, the temperature ranges from 135° C. to 165° C. and the pressure ranges from 3450 kPa (34.5 barg) to 10000 kPa (100 barg).

The source and purity of the hydrogen gas used in the processes of the present invention are not critical. The hydrogen gas used in the processes may comprise fresh hydrogen or a mixture of fresh hydrogen and recycled hydrogen. The hydrogen gas can be a mixture of hydrogen and, optionally, minor amounts, typically less than 30 mole %, of components such as CO and $CO_2$, and inert gases, such as argon, nitrogen, or methane. Typically, the hydrogen gas comprises at least 70 mole % of hydrogen. For example, the hydrogen gas comprises at least 90 mole % or, in another example, at least 97 mole %, of hydrogen. The hydrogen gas may be obtained from any of the conventional sources well known in the art such as, for example, by partial oxidation or steam reforming of natural gas. Pressure swing absorption can be used if a high purity hydrogen gas is desired. If hydrogen gas recycle is utilized in one of the processes, then the recycle hydrogen gas may contain minor amounts of one or more products of the hydrogenation reaction which have not been fully condensed in the product recovery stage downstream from the hydrogenation zone.

The hydrogenation of 2,2,4,4-tetraalkylcyclobutane-1,3-dione typically produces cis-2,2,4,4-tetraalkylcyclobutane-1,3-diol and trans-2,2,4,4-tetraalkylcyclobutane-1,3-diol. In certain embodiments of the present invention, the cis/trans molar ratio ranges from 0.8 to 0.4 or 0.7 to 0.4 or 0.6 to 0.4 or 0.5 to 0.4. In certain embodiments of the present invention, the cis/trans molar ratio ranges from 0.8 to 0.5 or 0.7 to 0.5 or 0.6 to 0.5. In certain embodiments of the present invention, the cis/trans molar ratio ranges from 0.8 to 0.6 or 0.7 to 0.6. In certain embodiments of the present invention, the cis/trans molar ratio ranges from 0.8 to 0.7.

The processes of this invention may be carried out in the absence or presence of a solvent, e.g., a solvent for the 2,2,4,4-tetraalkylcyclobutane-1,3-dione being hydrogenated which is compatible with the catalyst and the hydrogenation product or products. Examples of such solvents include alcohols such as methanol and ethanol; ethers, such as dimethyl ether and diethyl ether; glycols such as mono-, di- and tri-ethylene glycol; glycol ethers, such as ethylene glycol monobutyl ether and diethylene glycol monobutyl ether; saturated hydrocarbons such as hexane, cyclohexane, octane, and decane; and esters, such as isopropyl isobutyrate, isobutyl propionate, octyl acetate, isobutyl isobutyrate, isobutyl acetate, and the like. In one embodiment, the solvent is isobutyl isobutyrate. In one embodiment, the 2,2,4,4-tetraalkylcyclobutane-1,3-dione is dissolved in the solvent at a concentration of 1 to 60% (w/w), for example 5 to 50%, or 10 to 25%. In one embodiment in which the solvent is isobutyl isobutyrate, the 2,2,4,4-tetraalkylcyclobutane-1,3-dione is dissolved in the solvent at a concentration of 1 to 60% (w/w), for example 5 to 50%, or 10 to 25%. In certain embodiments, the hydrogenation process is conducted in the absence of solvent and use the neat, molten 2,2,4,4-tetraalkylcyclobutane-1,3-dione alone or as a mixture with the 2,2,4,4-tetraalkylcyclobutane-1,3-diol and other hydrogenation products, including 1-hydroxy-2,2,4-trimethyl-3-pentanone, 3-hydroxy-2,2,4,4-tetramethylcyclobutane-1-one, and 2,2,4-trimethyl-1,3-pentanediol, as the feed to the process.

Another embodiment of the present invention is drawn to a process to produce a 2,2,4,4-tetraalkylcyclobutane-1,3-diol comprising (1) feeding dialkylcarboxylic acid anhydride to a pyrolysis zone to produce a vapor effluent comprising dialkylketene, dialkylcarboxylic acid, and the unreacted dialkylcarboxylic acid anhydride; (2) cooling the vapor effluent to condense the dialkylcarboxylic acid and the dialkylcarboxylic acid anhydride and separating the condensate from the dialkylketene vapor; (3) feeding the dialkylketene vapor to an absorption zone wherein the dialkylketene vapor is dissolved in a solvent comprising an ester containing 4 to 20 carbon atoms and consisting of residues of an aliphatic carboxylic acid and an alkanol to produce an effluent comprising a solution of dialkylketene in the solvent; (4) feeding the absorption zone effluent to a dimerization zone wherein the effluent is heated to convert dialkylketene to 2,2,4,4-tetraalkylcyclobutane-1,3-dione to produce an effluent comprising a solution of 2,2,4,4-tetraalkylcyclobutane-1,3-dione in the solvent; and (5) contacting the 2,2,4,4-tetraalkylcyclobutane-1,3-dione with hydrogen in the presence of a cobalt-based catalyst under conditions of temperature and pressure sufficient to form a 2,2,4,4-tetraalkylcyclobutane-1,3-diol.

Another embodiment of the present invention is drawn to a process to produce a 2,2,4,4-tetraalkylcyclobutane-1,3-diol comprising (1) feeding a dialkyl carboxylic acid to a pyrolysis zone wherein the dialkyl carboxylic acid produces a vapor effluent comprising dialkylketene, water, and unreacted dialkyl carboxylic acid; (2) cooling the vapor effluent to condense water and dialkyl carboxylic acid and separating the condensate from the dialkylketene vapor; (3) feeding the dialkylketene vapor to an absorption zone wherein the dialkylketene vapor is dissolved in a solvent comprising an ester containing 4 to 20 carbon atoms and consisting of residues of an aliphatic carboxylic acid and an alkanol to produce an effluent comprising a solution of dialkylketene in the solvent; (4) feeding the absorption zone effluent to a dimerization zone wherein the effluent is heated to convert dialkylketene to 2,2,4,4-tetraalkylcyclobutane-1,3-dione to produce an effluent comprising a solution of 2,2,4,4-tetraalkylcyclobutane-1, 3-dione in the solvent; and (5) contacting the tetraalkylcyclobutane-1,3-dione with hydrogen in the presence of a cobalt-based catalyst under conditions of temperature and pressure sufficient to form a 2,2,4,4-tetraalkylcyclobutane-1, 3-diol.

The nature of the process for making the dialkylketene is not critical and any conventional method may be used, including, but not limited to, the methods disclosed in U.S. Pat. Nos. 1,602,699, 2,160,841, 2,202,046, 2,278,537, 2,806,064, 3,201,474, 3,259,469, 3,366,689, 3,403,181, 5,475,144 and 6,232,504, all of which are incorporated herein by reference for their disclosure of processes for making a dialkylketene. Processes for the preparation of ketenes, for example, dimethylketene, and tetraalkylcyclobutane-1,3-diones, for example, 2,2,4,4-tetramethylcyclobutane-1,3-dione, may be combined with all aspects of the present invention related to preparation of the 2,2,4,4-tetraalkylcyclobutane-1,3-diols, including mixtures of cis and trans-2,2,4,4-tetraalkylcyclobutane-1,3-diols.

All of these novel processes may be carried out as a batch, semi-continuous, or continuous process and may utilize a variety of reactor types. Examples of suitable reactor types include, but are not limited to, stirred tank, continuous stirred tank, slurry, tubular, fixed bed, and trickle bed. The term "continuous" as used herein means a process wherein reactants are introduced and products withdrawn simultaneously in an uninterrupted manner. By "continuous" it is meant that the process is substantially or completely continuous in operation, in contrast to a "batch" process. "Continuous" is not meant in any way to prohibit normal interruptions in the continuity of the process due to, for example, start-up, reactor maintenance, or scheduled shut down periods. The term "batch" process as used herein means a process wherein all the reactants are added to the reactor and then processed according to a predetermined course of reaction during which essentially no material is fed into or removed from the reactor. For example, in a batch operation, a slurry of the catalyst in the cyclobutanedione and/or a solvent in which the cyclobutanedione has been dissolved is fed to a pressure vessel equipped with means for agitation. The pressure vessel is then pressurized with hydrogen to a predetermined pressure followed by heating to bring the reaction mixture to the desired temperature. After the hydrogenation is complete, the reaction mixture is removed from the pressure vessel, the catalyst is separated by filtration, and the 2,2,4,4-tetramethylcyclobutane-1,3-diol product is isolated, for example, in a distillation train or by crystallization. The term "semicontinuous" means a process where some of the reactants are charged at the beginning of the process and the remaining reactants are fed continuously as the reaction progresses. Alternatively, a semi-continuous process may also include a process similar to a batch process in which all the reactants are added at the beginning of the process except that one or more of the products are removed continuously as the reaction progresses.

The process may be operated as a continuous process, although semi-continuous and batch processes are still within the scope of the invention. Continuous operation may utilize a fixed bed with a larger particle size of catalyst such as, for example, granules, pellets, various multilobal shaped pellets, rings, or saddles that are well known to skilled persons in the art. As an example of a continuous process, the catalyst bed may be fixed in a high pressure, tubular or columnar reactor and the liquid cyclobutanedione, dissolved in a solvent if necessary or desired, fed continuously into the top of the bed at elevated pressure and temperature, and the crude hydrogenation product removed from the base of the reactor. Alternatively, it is possible to feed the cyclobutanedione into the bottom of the bed and remove the crude product from the top of the reactor. It is also possible to use two or more catalyst beds or hydrogenation zones connected in parallel or in series to improve conversion, to reduce the quantity of catalyst, or to bypass a catalyst bed for periodic maintenance or catalyst removal. Another mode of continuous operation utilizes a slurry of the catalyst in an agitated pressure vessel, which is equipped with a filter leg to permit continuous removal of a solution of product in unreacted cyclobutanedione and/or a solvent. In this manner, a liquid reactant or reactant solution can be continuously fed to, and product solution continuously removed from, an agitated pressure vessel containing an agitated slurry of the catalyst.

In one embodiment, the present invention provides processes for producing a 2,2,4,4-tetraalkylcyclobutane-1,3-diol of Formula II, comprising contacting a 2,2,4,4-tetraalkylcyclobutane-1,3-dione with hydrogen in the presence of a cobalt-based catalyst under conditions of temperature and pressure sufficient to form a 2,2,4,4-tetraalkylcyclobutane-1, 3-diol, wherein the alkyl radicals $R_1$, $R_2$, $R_3$ and $R_4$ each independently have 1 to 8 carbon atoms.

In one embodiment, the present invention provides processes for producing a 2,2,4,4-tetraalkylcyclobutane-1,3-diol of Formula II, comprising contacting a 2,2,4,4-tetraalkylcyclobutane-1,3-dione with hydrogen in the presence of a cobalt-based catalyst under conditions of temperature and pressure sufficient to form a 2,2,4,4-tetraalkylcyclobutane-1, 3-diol. In one embodiment, the alkyl radical radicals $R_1$, $R_2$, $R_3$ and $R_4$ each independently have 1 to 4 carbon atoms. In one embodiment, the alkyl radical radicals $R_1$, $R_2$, $R_3$ and $R_4$ each are methyl groups. In one embodiment, the 2,2,4,4-tetraalkylcyclobutane-1,3-diol is 2,2,4,4-tetramethylcyclobutane-1,3-diol. In one embodiment, the 2,2,4,4-tetraalkylcyclobutane-1,3-dione is 2,2,4,4-tetramethylcyclobutane-1, 3-dione.

In one embodiment, the present invention provides processes for producing a 2,2,4,4-tetraalkylcyclobutane-1,3-diol of Formula II, comprising contacting a 2,2,4,4-tetraalkylcyclobutane-1,3-dione with hydrogen in the presence of a cobalt-based catalyst under conditions of temperature and pressure sufficient to form a 2,2,4,4-tetraalkylcyclobutane-1, 3-diol, wherein the alkyl radicals $R_1$, $R_2$, $R_3$ and $R_4$ each independently have 1 to 8 carbon atoms and wherein the process further comprises a non-protic solvent. In one embodiment, the non-protic solvent comprises an unsaturated hydrocarbon, a non-cyclic ester, i.e., not a lactone, or ether. The term "non-cyclic ester" means the ester is not a lactone, although the alkanol or aliphatic carboxylic acid residues of the ester may have one or more cyclic rings. In one embodiment, the non-cyclic ester contains 4 to 20 carbon atoms and comprises at least one residue of an aliphatic carboxylic acid and at least one residue of an alkanol. In one embodiment, the non-cyclic ester is selected from isopropyl isobutyrate, isobutyl propionate, octyl acetate, isobutyl isobutyrate, isobutyl acetate, and mixtures thereof.

In one embodiment, the present invention provides processes for producing a 2,2,4,4-tetraalkylcyclobutane-1,3-diol of Formula II, comprising contacting a 2,2,4,4-tetraalkylcyclobutane-1,3-dione with hydrogen in the presence of a cobalt-based catalyst under conditions of temperature and pressure sufficient to form a 2,2,4,4-tetraalkylcyclobutane-1,3-diol, wherein the alkyl radicals $R_1$, $R_2$, $R_3$ and $R_4$ each independently have 1 to 8 carbon atoms and wherein the process further comprises a protic solvent. In one embodiment, the protic solvent comprises one or more solvents chosen from a monohydric alcohol, a dihydric alcohol, and a polyhydric alcohol. In one embodiment, the protic solvent comprises one or more solvents chosen from a monohydric alcohol and a dihydric alcohol. In one embodiment, the protic solvent comprises methanol and ethylene glycol.

In one embodiment, the present invention provides processes for producing a 2,2,4,4-tetraalkylcyclobutane-1,3-diol of Formula II, comprising contacting a 2,2,4,4-tetraalkylcyclobutane-1,3-dione with hydrogen in the presence of a cobalt-based catalyst under conditions of temperature and pressure sufficient to form a 2,2,4,4-tetraalkylcyclobutane-1,3-diol, wherein the alkyl radicals $R_1$, $R_2$, $R_3$ and $R_4$ each independently have 1 to 8 carbon atoms and wherein the cobalt-based catalyst comprises a support. In one embodiment, the support comprises one or more of silica, alumina, aluminosilicate, silica/alumina, kieselguhr, titania, graphite, silicon carbide, carbon, zirconia, chromate, barium chromate, zinc oxide, clay, and alumina-clay. In one embodiment, the support comprises a form selected from powder, extrudate, spheres, and pellets.

In one embodiment, the present invention provides processes for producing a 2,2,4,4-tetraalkylcyclobutane-1,3-diol of Formula II, comprising contacting a 2,2,4,4-tetraalkylcyclobutane-1,3-dione with hydrogen in the presence of a cobalt-based catalyst under conditions of temperature and pressure sufficient to form a 2,2,4,4-tetraalkylcyclobutane-1,3-diol, wherein the alkyl radicals $R_1$, $R_2$, $R_3$ and $R_4$ each independently have 1 to 8 carbon atoms and wherein the pressure ranges from 689 kPa (100 psi) to 41,368 kPa (6000 psi). In one embodiment, the pressure ranges from 1380 kPa (200 psi) to 20,684 kPa (3000 psi). In one embodiment, the pressure ranges from 2068 kPa (300 psi) to 14,789 kPa (2000 psi). In one embodiment, the temperature ranges from 75° C. to 250° C. In one embodiment, the temperature ranges from 120° C. to 200° C. In one embodiment, the temperature ranges from 130° C. to 180° C.

In one embodiment, the present invention provides processes for producing a 2,2,4,4-tetraalkylcyclobutane-1,3-diol of Formula II, comprising contacting a 2,2,4,4-tetraalkylcyclobutane-1,3-dione with hydrogen in the presence of a cobalt-based catalyst under conditions of temperature and pressure sufficient to form a 2,2,4,4-tetraalkylcyclobutane-1,3-diol, wherein the alkyl radicals $R_1$, $R_2$, $R_3$ and $R_4$ each independently have 1 to 8 carbon atoms and wherein the 2,2,4,4-tetraalkylcyclobutane-1,3-diol comprises cis-2,2,4,4-tetramethylcyclobutane-1,3-diol and trans-2,2,4,4-tetramethylcyclobutane-1,3-diol and the 2,2,4,4-tetramethylcyclobutane-1,3-diol has a cis/trans molar ratio of 0.4 to 0.8. In one embodiment, the 2,2,4,4-tetramethylcyclobutane-1,3-diol has a cis/trans molar ratio ranging from 0.4 to 0.7.

In one embodiment, the present invention provides processes for producing a 2,2,4,4-tetraalkylcyclobutane-1,3-diol of Formula II, comprising contacting a 2,2,4,4-tetraalkylcyclobutane-1,3-dione with hydrogen in the presence of a cobalt-based catalyst under conditions of temperature and pressure sufficient to form a 2,2,4,4-tetraalkylcyclobutane-1,3-diol, wherein the alkyl radicals $R_1$, $R_2$, $R_3$ and $R_4$ each independently have 1 to 8 carbon atoms and wherein the 2,2,4,4-tetramethylcyclobutane-1,3-dione, the 2,2,4,4-tetramethylcyclobutane-1,3-diol, or both are in the molten liquid phase, i.e., no solvent.

In one embodiment, the present invention provides processes for producing 2,2,4,4-tetramethylcyclobutane-1,3-diol, comprising contacting 2,2,4,4-tetramethylcyclobutane-1,3-dione, a cobalt-based catalyst, a non-protic solvent, and hydrogen in a hydrogenation zone under conditions of temperature and pressure sufficient to form 2,2,4,4-tetramethylcyclobutane-1,3-diol. In one such embodiment, the 2,2,4,4-tetramethylcyclobutane-1,3-dione and hydrogen are continuously fed into the hydrogenation zone. In one such embodiment, the hydrogenation zone has a temperature ranging from 75° C. to 250° C. In one such embodiment, the pressure ranges from 689 kPa (100 psi) to 41,368 kPa (6000 psi).

In one embodiment, the present invention provides processes for producing 2,2,4,4-tetramethylcyclobutane-1,3-diol, comprising contacting 2,2,4,4-tetramethylcyclobutane-1,3-dione, a cobalt-based catalyst, a non-protic solvent, and hydrogen in a hydrogenation zone under conditions of temperature and pressure sufficient to form 2,2,4,4-tetramethylcyclobutane-1,3-diol, and further comprising continuously recovering an effluent comprising the 2,2,4,4-tetramethylcyclobutane-1,3-diol and the solvent from the hydrogenation zone. In one such embodiment, the process further comprises continuously recycling a portion of the effluent to the hydrogenation zone. In one such embodiment, the process further comprises continuously recovering the effluent from the hydrogenation zone and recovering at least a portion of the 2,2,4,4-tetramethylcyclobutane-1,3-diol from the effluent to form a depleted 2,2,4,4-tetramethylcyclobutane-1,3-diol stream. In one such embodiment, at least a portion of the depleted 2,2,4,4-tetramethylcyclobutane-1,3-diol stream is recycled to the hydrogenation zone. The term "depleted 2,2,4,4-tetramethylcyclobutane-1,3-diol stream" means a stream having less 2,2,4,4-tetramethylcyclobutane-1,3-diol than the effluent from which the depleted 2,2,4,4-tetramethylcyclobutane-1,3-diol stream is derived. In one such embodiment, the hydrogenation zone comprises a tubular, fixed bed, or trickle bed reactor. In one such embodiment, the hydrogenation zone comprises a stirred tank, a continuous stirred tank, or a slurry reactor. In one such embodiment, the 2,2,4,4-tetramethylcyclobutane-1,3-diol has a cis/trans molar ratio of 0.9 or less. In one such embodiment, the 2,2,4,4-tetramethylcyclobutane-1,3-diol has a cis/trans molar ratio of 0.3 or more.

In one embodiment, the present invention provides processes for producing 2,2,4,4-tetramethylcyclobutane-1,3-diol comprising (1) feeding isobutyric anhydride to a pyrolysis zone, wherein the isobutyric anhydride is heated at a temperature of 350 to 600° C. to produce a vapor effluent comprising dimethylketene, isobutyric acid, and unreacted isobutyric anhydride; (2) cooling the vapor effluent to condense isobutyric acid and isobutyric anhydride and separating the condensate from the dimethylketene vapor; (3) feeding the dimethylketene vapor to an absorption zone, wherein the dimethylketene vapor is contacted with and dissolved in a solvent comprising an ester containing 4 to 20 carbon atoms and consisting of residues of an aliphatic carboxylic acid and an alkanol to produce an effluent comprising a solution of dimethylketene in the solvent; (4) feeding the absorption zone effluent to a dimerization zone wherein the effluent is heated at a temperature ranging from 70 to 140° C. to convert dimethylketene to 2,2,4,4-tetramethylcyclobutane-1,3-dione to produce an effluent comprising a solution of 2,2,4,4-tetramethylcyclobutane-1,3-dione in the solvent; and (5) contacting the 2,2,4,4-tetramethylcyclobutane-1,3-dione with hydrogen in the presence of a cobalt-based catalyst under conditions of temperature and pressure sufficient to form a 2,2,4,4-tetramethylcyclobutane-1,3-diol.

In one embodiment, the present invention provides processes for producing a 2,2,4,4-tetraalkylcyclobutane-1,3-diol of Formula II, comprising contacting a 2,2,4,4-tetraalkylcyclobutane-1,3-dione with hydrogen in the presence of a non-promoted cobalt-based catalyst, the catalyst comprising an alumina support, under conditions of temperature and pressure sufficient to form a 2,2,4,4-tetraalkylcyclobutane-1,3-diol, wherein the alkyl radicals $R_1$, $R_2$, $R_3$ and $R_4$ each have 1 carbon atom, wherein the temperature ranges from 150° C. to 180° C., for example 160° C. to 170° C., wherein the pressure ranges from 34.5 to 100 barg, and wherein the cis/trans molar ratio of the 2,2,4,4-tetraalkylcyclobutane-1,3-diol is greater than 0.50, for example from 0.50 to 0.60.

In one embodiment, the present invention provides processes for producing a 2,2,4,4-tetraalkylcyclobutane-1,3-diol of Formula II, comprising contacting a 2,2,4,4-tetraalkylcyclobutane-1,3-dione with hydrogen in the presence of a non-promoted cobalt-based catalyst, the catalyst comprising an alumina support, under conditions of temperature and pressure sufficient to form a 2,2,4,4-tetraalkylcyclobutane-1,3-diol, wherein the alkyl radicals $R_1$, $R_2$, $R_3$ and $R_4$ each have 1 carbon atom, wherein the temperature ranges from 120° C. to 150° C., for example 130° C. to 140° C., wherein the pressure ranges from 34.5 to 100 barg, and wherein the cis/trans molar ratio of the 2,2,4,4-tetraalkylcyclobutane-1,3-diol is less than 0.5, for example from 0.4 to 0.45.

In one embodiment, the present invention provides processes for producing a 2,2,4,4-tetraalkylcyclobutane-1,3-diol of Formula II, comprising contacting a 2,2,4,4-tetraalkylcyclobutane-1,3-dione with hydrogen in the presence of a non-promoted cobalt-based catalyst, the catalyst comprising an alumina support, under conditions of temperature and pressure sufficient to form a 2,2,4,4-tetraalkylcyclobutane-1,3-diol, wherein the alkyl radicals $R_1$, $R_2$, $R_3$ and $R_4$ each have 1 carbon atom, wherein the temperature ranges from 150° C. to 180° C., for example 160° C. to 170° C., wherein the pressure ranges from 34.5 to 100 barg, and wherein the conversion of a 2,2,4,4-tetraalkylcyclobutane-1,3-dione to the 2,2,4,4-tetraalkylcyclobutane-1,3-diol is at least 90%, or greater than 95%, or greater than 99% and the yield of the 2,2,4,4-tetraalkylcyclobutane-1,3-diol is greater than 75%, or greater than 85%, or from 77% to 90%.

In one embodiment, the present invention provides processes for producing a 2,2,4,4-tetraalkylcyclobutane-1,3-diol of Formula II, comprising contacting a 2,2,4,4-tetraalkylcyclobutane-1,3-dione with hydrogen in the presence of a non-promoted cobalt-based catalyst, the catalyst comprising a silica support, under conditions of temperature and pressure sufficient to form a 2,2,4,4-tetraalkylcyclobutane-1,3-diol, wherein the alkyl radicals $R_1$, $R_2$, $R_3$ and $R_4$ each have 1 carbon atom, wherein the temperature ranges from 120° C. to 180° C., or 130° C. to 170° C., or 135° C. to 165° C. wherein the pressure ranges from 34.5 to 100 barg, and wherein the conversion of a 2,2,4,4-tetraalkylcyclobutane-1,3-dione to the 2,2,4,4-tetraalkylcyclobutane-1,3-diol is at least 90%, or from 90 to 99%, the selectivity ranges from 80 to 90%, the yield of the 2,2,4,4-tetraalkylcyclobutane-1,3-diol is 65 to 85% or 67 to 84% and the cis/trans molar ratio ranges from 0.60 to 0.75, or 0.60 to 0.73, or 0.63 to 0.73.

In one embodiment, the present invention provides processes for producing a 2,2,4,4-tetraalkylcyclobutane-1,3-diol of Formula II, comprising contacting a 2,2,4,4-tetraalkylcyclobutane-1,3-dione with hydrogen in the presence of a non-promoted cobalt-based catalyst, the catalyst comprising a silica/alumina support, under conditions of temperature and pressure sufficient to form a 2,2,4,4-tetraalkylcyclobutane-1,3-diol, wherein the alkyl radicals $R_1$, $R_2$, $R_3$ and $R_4$ each have 1 carbon atom, wherein the temperature ranges from 120° C. to 180° C., 130° C. to 170° C. or 135° C. to 165° C., wherein the conversion of a 2,2,4,4-tetraalkylcyclobutane-1,3-dione to the 2,2,4,4-tetraalkylcyclobutane-1,3-diol is at least 70%, or 70 to 83%, or 70 to 96% or 83 to 96% and the cis/trans molar ratio is at least 0.75 or from 0.75 to 0.80.

In one embodiment, the present invention provides processes for making 2,2,4,4-tetramethylcyclobutane-1,3-diol comprising continuously feeding 2,2,4,4-tetramethylcyclobutane-1,3-dione, a non-protic solvent, and hydrogen to a hydrogenation zone comprising a cobalt-based catalyst at pressure of 689 kPa (100 psi) (7 bar) to 41,368 kPa (6000 psi) (420 bar) and a hydrogenation temperature of 75° C. to 250° C. and continuously recovering from said hydrogenation zone an effluent comprising 2,2,4,4-tetramethylcyclobutane-1,3-diol and the non-protic solvent. In another embodiment, the process may further comprise continuously recycling a portion of the effluent to the hydrogenation zone. The hydrogenation zone may be any suitable reactor type including, but not limited to, stirred tank, continuous stirred tank, slurry, tubular, fixed bed, and trickle bed. For example, the processes of the invention may be carried out in a trickle bed reactor operated in the molten liquid phase. Certain embodiments of the invention are further described and illustrated by the following examples.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the claims below.

Further embodiments of the invention include:

A process for producing a 2,2,4,4-tetraalkylcyclobutane-1,3-diol of Formula II, comprising contacting a 2,2,4,4-tetraalkylcyclobutane-1,3-dione with hydrogen in the presence of a cobalt-based catalyst under conditions of temperature and pressure sufficient to form a 2,2,4,4-tetraalkylcyclobutane-1,3-diol,

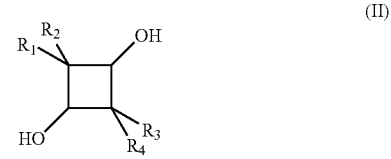

(II)

wherein each of the alkyl radicals $R_1$, $R_2$, $R_3$ and $R_4$ has, independently from each other, 1 to 8 carbon atoms; and wherein the cis/trans molar ratio of the 2,2,4,4-tetraalkylcyclobutane-1,3-diol is from 0.4 to 0.8.

The process according to any of the applicable preceding embodiments, wherein each of the alkyl radical radicals $R_1$, $R_2$, $R_3$, and $R_4$ has, independently from each other, 1 to 4 carbon atoms.

The process according to any of the applicable preceding embodiments, wherein each alkyl radical $R_1$, $R_2$, $R_3$, and $R_4$ is a methyl group.

The process according to any of the applicable preceding embodiments, wherein the 2,2,4,4-tetraalkylcyclobutane-1,3-dione is 2,2,4,4-tetramethylcyclobutane-1,3-dione.

The process according to any of the applicable preceding embodiments, wherein a non-protic solvent comprising an unsaturated hydrocarbon, a non-cyclic ester, or an ether, is present during the formation of the 2,2,4,4-tetraalkylcyclobutane-1,3-diol.

The process according to any of the applicable preceding embodiments, wherein the non-cyclic ester contains 4 to 20 carbon atoms and comprises at least one residue of an aliphatic carboxylic acid and at least one residue of an alkanol.

The process according to any of the applicable preceding embodiments, wherein the non-cyclic ester is chosen from isopropyl isobutyrate, isobutyl propionate, octyl acetate, isobutyl isobutyrate, isobutyl acetate, and mixtures thereof.

The process according to any of the applicable preceding embodiments, wherein a protic solvent comprising one or more solvents chosen from a monohydric alcohol, a dihydric alcohol, a polyhydric alcohol, and mixtures thereof is present during the formation of the 2,2,4,4-tetraalkylcyclobutane-1,3-diol.

The process according to any of the applicable preceding embodiments, wherein the protic solvent comprises methanol or ethylene glycol.

The process according to any of the applicable preceding embodiments, wherein the cobalt-based catalyst comprises a support, and wherein the support comprises one or more of silica, alumina, or silica/alumina.

The process according to any of the applicable preceding embodiments, wherein the support comprises a form chosen from powder, extrudate, spheres, and pellets.

The process according to any of the applicable preceding embodiments, wherein the pressure is from 100 psi to 6000 psi.

The process according to any of the applicable preceding embodiments, wherein the pressure is from 1380 kPa (200 psi) to 20,684 kPa (3000 psi).

The process according to any of the applicable preceding embodiments, wherein the pressure is from 300 psi to 2000 psi.

The process according to any of the applicable preceding embodiments, wherein the temperature is from 75° C. to 250° C.

The process according to any of the applicable preceding embodiments, wherein the temperature is from 120° C. to 200° C.

The process according to any of the applicable preceding embodiments, wherein the temperature is from 130° C. to 180° C.

The process according to any of the applicable preceding embodiments, wherein the temperature is from 100° C. to 180° C.

The process according to any of the applicable preceding embodiments, wherein the process is a continuous, semi-batch, or batch process.

The process according to any of the applicable preceding embodiments, wherein the 2,2,4,4-tetraalkylcyclobutane-1,3-diol comprises cis-2,2,4,4-tetramethylcyclobutane-1,3-diol and trans-2,2,4,4-tetramethylcyclobutane-1,3-diol and the 2,2,4,4-tetramethylcyclobutane-1,3-diol has a cis/trans molar ratio of 0.3 to 1.7.

The process according to any of the applicable preceding embodiments, wherein the 2,2,4,4-tetramethylcyclobutane-1,3-diol has a cis/trans molar ratio of 0.3 to 1.1.

The process according to any of the applicable preceding embodiments, wherein the 2,2,4,4-tetramethylcyclobutane-1,3-diol has a cis/trans molar ratio of 0.3 to 0.9.

The process according to any of the applicable preceding embodiments, wherein the 2,2,4,4-tetramethylcyclobutane-1,3-dione, the 2,2,4,4-tetramethylcyclobutane-1,3-diol, or both are in the molten liquid phase.

A process for producing 2,2,4,4-tetramethylcyclobutane-1,3-diol, comprising contacting 2,2,4,4-tetramethylcyclobutane-1,3-dione, a cobalt-based catalyst, a non-protic solvent, and hydrogen in a hydrogenation zone under conditions of temperature and pressure sufficient to form 2,2,4,4-tetramethylcyclobutane-1,3-diol; wherein the cis/trans molar ratio of the 2,2,4,4-tetramethylcyclobutane-1,3-diol is from 0.4 to 0.8.

The process according to any of the applicable preceding embodiments, wherein the 2,2,4,4-tetramethylcyclobutane-1,3-dione and hydrogen are continuously fed into the hydrogenation zone.

The process according to any of the applicable preceding embodiments, wherein the hydrogenation zone has a temperature from 75° C. to 250° C.

The process according to any of the applicable preceding embodiments, wherein the pressure is from 100 psi to 6000 psi.

The process according to any of the applicable preceding embodiments, further comprising continuously recovering an effluent comprising the 2,2,4,4-tetramethylcyclobutane-1,3-diol and the solvent from the hydrogenation zone.

The process according to any of the applicable preceding embodiments, further comprising continuously recycling a portion of the effluent to the hydrogenation zone.

The process according to any of the applicable preceding embodiments, further comprising continuously recovering the effluent from the hydrogenation zone and recovering at least a portion of the 2,2,4,4-tetramethylcyclobutane-1,3-diol from the effluent to form a depleted 2,2,4,4-1,3-tetramethylcyclobutane-1,3-diol stream.

The process according to any of the applicable preceding embodiments, wherein at least a portion of the depleted 2,2,4,4-1,3-tetramethylcyclobutane-1,3-diol stream is recycled to the hydrogenation zone.

The process according to any of the applicable preceding embodiments, wherein the hydrogenation zone comprises a tubular reactor, a fixed bed reactor, a trickle bed reactor, a stirred tank reactor, a continuous stirred tank reactor, or a slurry reactor.

The process according to any of the applicable preceding embodiments, wherein the 2,2,4,4-tetramethylcyclobutane-1,3-diol has a cis/trans molar ratio of 1.3 or less.

The process according to any of the applicable preceding embodiments, wherein the 2,2,4,4-tetramethylcyclobutane-1,3-diol has a cis/trans molar ratio of 0.3 or more.

The process according to any of the applicable preceding embodiments, wherein the 2,2,4,4-tetramethylcyclobutane-1,3-diol has a cis/trans molar ratio of 0.3-1.7.

A process for producing 2,2,4,4-tetramethylcyclobutane-1,3-diol comprising:
(a) feeding isobutyric anhydride to a pyrolysis zone, wherein the isobutyric anhydride is heated at a temperature of 350° C. to 600° C. to produce a vapor effluent comprising dimethylketene, isobutyric acid, and unreacted isobutyric anhydride;
(b) cooling the vapor effluent to condense isobutyric acid and isobutyric anhydride and separating the condensate from the dimethylketene vapor;

(c) feeding the dimethylketene vapor to an absorption zone, wherein the dimethylketene vapor is contacted with a solvent comprising an ester containing 4 to 20 carbon atoms to produce an absorption zone effluent comprising a solution of dimethylketene in the solvent; wherein the ester comprises residues of an aliphatic carboxylic acid and an alkanol;

(d) feeding the absorption zone effluent to a dimerization zone wherein the absorption zone effluent is heated at a temperature of from 70° C. to 140° C. to convert dimethylketene to 2,2,4,4-tetramethylcyclobutane-1,3-dione to produce an effluent comprising a solution of 2,2,4,4-tetramethylcyclobutane-1,3-dione in the solvent; and (e) contacting the 2,2,4,4-tetramethylcyclobutane-1,3-dione with hydrogen in the presence of a cobalt-based catalyst under conditions of temperature and pressure sufficient to form a 2,2,4,4-tetramethylcyclobutane-1,3-diol;
wherein the cis/trans molar ratio of the 2,2,4,4-tetramethylcyclobutane-1,3-diol is from 0.4 to 0.8.

The processes according to any of the applicable preceding embodiments, further comprising continuously recovering the effluent from the hydrogenation zone and recovering at least a portion of the 2,2,4,4-tetramethylcyclobutane-1,3-diol from the effluent to form a 2,2,4,4-tetramethylcyclobutane-1,3-diol-depleted stream. A 2,2,4,4-tetramethylcyclobutane-1,3-diol-depleted stream has less 2,2,4,4-tetramethylcyclobutane-1,3-diol that the effluent recovered from the hydrogenation zone.

In certain embodiments of the hydrogenation process, the conversion of the 2,2,4,4-tetramethylcyclobutane-1,3-dione to 2,2,4,4-tetramethylcyclobutane-1,3-diol ranges from 75 to 100 mol %, greater than 75 to 100 mol %, greater than 76 to 100 mol %, or 90 to 100 mol %. In certain embodiments of the hydrogenation process, the selectivity of the 2,24,4-tetramethylcyclobutane-1,3-dione to 2,24,4-tetramethylcyclobutane-1,3-diol ranges from 65 to 90 mol %, 65 to 77 mol %, greater than 75 to 90 mol %, 77 to 90 mol %, 82 to 90 mol % or greater than 65 to 90 mol %.

EXAMPLES

The following examples illustrate in general the processes of the present invention for the production of 2,2,4,4-tetraalkylcyclobutane-1,3-diols by hydrogenation of 2,2,4,4-tetraalkylcyclobutane-1,3-dione.

General

The following is a general description of the reactor system, catalyst preparation, hydrogenation process, and analytical methods used henceforward in the Examples unless otherwise specified.

The experiments were performed in a nanoflow parallel fixed bed reactor system under continuous trickle phase conditions in co-current downstream mode utilizing a tubular reactor that has an internal diameter of 2 mm. The reactor is made by Advantium Technologies B.V. The reactor was loaded with solid catalyst to fill a volume of 150 μl. The catalyst was reduced with hydrogen in-situ prior to testing. The catalyst reduction was carried out in the presence of isobutyl isobutyrate at 100 barg (10,000 kPa). Temperature was increased at a rate of 0.5° C./min from ambient temperature to 180° C. and held for 2 hours, which was considered to be the reaction time.

The 2,2,4,4-tetramethylcyclobutane-1,3-dione used in the experiments was diluted with isobutyl isobutyrate to a concentration of 10 wt % and heated to 85° C. The 2,2,4,4-tetramethylcyclobutane-1,3-dione/isobutyl isobutyrate feed mixture was fed at the top of the reactor vessel along with hydrogen and contacted with the catalyst. After the system reached the correct process conditions, the system was held at these conditions for 2 hours. The reactor effluent stream containing crude 2,2,4,4-tetramethylcyclobutane-1,3-diol product was removed from the bottom of the reactor.

The reactor effluent stream was sampled using a Gilson 233 liquid sampler. 30 μl of the reaction sample was diluted with 970 μl isopropanol and analyzed by capillary gas-liquid chromatography ("GC") using a TraceGC from Thermo Finnigan with a CombiPal autosampler from CTC Analytics, with a FID detector. The GC samples were injected onto a 0.25 micron (30 m×0.32 mm) Varian CP Wax 52 CB column. For each analysis, the initial temperature of the column was set at 80° C., held for 2 minutes, ramped to 90° C. at a rate of 5° C./min, ramped to 240° C. at a rate of 20° C./min, and then held for 3.5 min at 240° C. Results are given as GC area percentages, normalized for isobutyl isobutyrate.

The following abbreviations apply throughout the working examples and tables:

| | |
|---|---|
| TMCB | 2,2,4,4-tetramethylcyclobutane-1,3-dione |
| Ring-open Ketol | 1-hydroxy-2,2,4-trimethyl-3-pentanone (a product of the partial hydrogenation and ring opening of 2,2,4,4-tetramethylcyclobutane-1,3-dione) |
| Cyclic Ketol | 3-hydroxy-2,2,4,4-tetramethylcyclobutanone (a product of the partial hydrogenation of 2,2,4,4-tetramethylcyclobutane-1,3-dione) |
| TMPD | 2,2,4-trimethyl-1,3-pentanediol (a product of the hydrogenation of Ring-opened Ketol) |
| Cis-Diol | cis-2,2,4,4-tetramethylcyclobutane-1,3-diol |
| Trans-Diol | trans-2,2,4,4-tetramethylcyclobutane-1,3-diol |

The conversion, selectivity, and yield of the hydrogenation process as well as the cis:trans ratio of the 2,2,4,4-tetramethylcyclobutane-1,3-diol product were calculated on the basis of GC area percentages using the following formulas:

$$\text{Conversion \%} = \frac{(\text{moles } TMCB \text{ fed}) - (\text{moles } TMCB \text{ remaining})}{(\text{moles } TMCB \text{ fed})} \times 100$$

$$\text{Yield \%} = \frac{(\text{moles } Cis-Diol) + (\text{moles } Trans-Diol)}{(\text{moles } TMCB \text{ fed})} \times 100$$

$$\text{Selectivity} = \frac{(\text{moles } Cis-Diol) + (\text{moles } Trans-Diol)}{(\text{moles } TMCB \text{ fed}) - (\text{moles } TMCB \text{ remaining})} = \frac{\text{Yield}}{\text{Conversion}}$$

$$Cis/Trans \text{ Ratio} = \frac{(\text{moles } Cis-Diol)}{(\text{moles } Trans-Diol)}$$

Example 1

Using the general procedure described above, 2,2,4,4-tetramethylcyclobutane-1,3-dione was hydrogenated using a supported cobalt catalyst at temperatures of 135° C. and 165° C., reactor pressures of 34.5 barg (3450 kPa) and 100 barg (10,000 kPa), and a liquid space velocity of 25 hr$^{-1}$. The catalyst used was an A280 cobalt on alumina catalyst obtained from Engelhard Corporation. The results are shown in Table 1.

TABLE 1

Hydrogenation of 2,2,4,4-tetramethylcyclobutane-1,3-dione using a cobalt catalyst.

| | Example | | | |
|---|---|---|---|---|
| | 1a | 1b | 1c | 1d |
| Support | alumina | alumina | alumina | alumina |
| Temperature (° C.) | 135 | 135 | 165 | 165 |
| Pressure (barg) | 34.5 | 100 | 34.5 | 100 |
| TMCB % | 22.9 | 10.4 | 0 | 0 |
| Ring-Open Ketol % | 1.2 | 1.4 | 5.6 | 5.8 |
| Cyclic Ketol % | 67.6 | 71.5 | 11.8 | 7.2 |
| TMPD % | 0 | 0 | 5.1 | 4.0 |
| Cis-Diol % | 2.5 | 5.1 | 27.0 | 28.8 |
| Trans-Diol % | 5.9 | 11.7 | 50.5 | 54.2 |
| Conversion % | 76.8 | 89.5 | 100 | 100 |
| Selectivity % | 8.3 | 16.6 | 77.4 | 82.9 |
| Yield % | 6.3 | 14.8 | 77.4 | 82.9 |
| Cis/Trans | 0.42 | 0.44 | 0.54 | 0.53 |

Example 2

Using the general procedure described above, 2,2,4,4-tetramethylcyclobutane-1,3-dione was hydrogenated using a supported cobalt catalyst at temperatures of 135° C. and 165° C., reactor pressures of 34.5 barg (3450 kPa) and 100 barg (10,000 kPa), and a liquid space velocity of 25 $hr^{-1}$. The catalyst used was an A281 cobalt on alumina catalyst obtained from Engelhard Corporation. The results are shown in Table 2.

TABLE 2

Hydrogenation of 2,2,4,4-tetramethylcyclobutane-1,3-dione using a cobalt catalyst.

| | Example | | | |
|---|---|---|---|---|
| | 2a | 2b | 2c | 2d |
| Support | alumina | alumina | alumina | alumina |
| Temperature (° C.) | 135 | 135 | 165 | 165 |
| Pressure (barg) | 34.5 | 100 | 34.5 | 100 |
| TMCB % | 23.6 | 7.6 | 0 | 0 |
| Ring-Open Ketol % | 1.3 | 1.1 | 3.5 | 3.1 |
| Cyclic Ketol % | 63.9 | 65.1 | 5.9 | 2.0 |
| TMPD % | 0 | 0 | 5.9 | 5.2 |
| Cis-Diol % | 3.1 | 7.8 | 31.2 | 32.2 |
| Trans-Diol % | 7.6 | 17.8 | 53.5 | 56.9 |
| Conversion % | 75.9 | 92.3 | 100 | 100 |
| Selectivity % | 10.5 | 25.5 | 84.7 | 89.7 |
| Yield % | 8.0 | 23.5 | 84.7 | 89.7 |
| Cis/Trans | 0.41 | 0.44 | 0.58 | 0.56 |

Example 3

Using the general procedure described above, 2,2,4,4-tetramethylcyclobutane-1,3-dione was hydrogenated using a supported cobalt catalyst at temperatures of 135° C. and 165° C., reactor pressures of 34.5 barg (3450 kPa) and 100 barg (10,000 kPa), and a liquid space velocity of 25 $hr^{-1}$. The catalyst used was a G-67A 20% cobalt on silica catalyst obtained from Süd-Chemie. The results are shown in Table 3.

TABLE 3

Hydrogenation of 2,2,4,4-tetramethylcyclobutane-1,3-dione using a cobalt catalyst.

| | Example | | | |
|---|---|---|---|---|
| | 3a | 3b | 3c | 3d |
| Support | silica | silica | silica | silica |
| Temperature (° C.) | 135 | 135 | 165 | 165 |
| Pressure (barg) | 34.5 | 100 | 34.5 | 100 |
| TMCB % | 6.5 | 7.5 | 0.8 | 0 |
| Ring-Open Ketol % | 0 | 0.7 | 3.8 | 18.7 |
| Cyclic Ketol % | 1.3 | 0.7 | 2.3 | 8.2 |
| TMPD % | 2.3 | 2.2 | 11.8 | 6.2 |
| Cis-Diol % | 33.6 | 34.1 | 34.3 | 26.9 |
| Trans-Diol % | 56.3 | 54.3 | 47.0 | 40.1 |
| Conversion % | 93.3 | 92.2 | 99.2 | 100 |
| Selectivity % | 89.8 | 88.7 | 81.4 | 67.0 |
| Yield % | 83.8 | 81.8 | 80.8 | 67.0 |
| Cis/Trans | 0.60 | 0.63 | 0.73 | 0.67 |

Example 4

Using the general procedure described above, 2,2,4,4-tetramethylcyclobutane-1,3-dione was hydrogenated using a a supported cobalt catalyst at temperatures of 135° C. and 165° C., reactor pressures of 34.5 barg (3450 kPa) and 100 barg (10,000 kPa), and a liquid space velocity of 25 $hr^{-1}$. The catalyst used was a T4405 57% cobalt on silica/alumina catalyst obtained from Süd-Chemie. The results are shown in Table 4.

TABLE 4

Hydrogenation of 2,2,4,4-tetramethylcyclobutane-1,3-dione using a cobalt catalyst.

| | Example | | | |
|---|---|---|---|---|
| | 5a | 5b | 5c | 5d |
| Support | silica/alumina | silica/alumina | silica/alumina | silica/alumina |
| Temperature (° C.) | 135 | 135 | 165 | 165 |
| Pressure (barg) | 34.5 | 100 | 34.5 | 100 |
| TMCB % | 29.4 | 59.3 | 16.5 | 3.9 |
| Ring-Open Ketol % | 2.5 | 1.4 | 15.6 | 15.9 |
| Cyclic Ketol % | 63.3 | 37.6 | 59.3 | 60.1 |
| TMPD % | 0 | 0 | 0 | 0 |
| Cis-Diol % | 1.8 | 0 | 3.1 | 8.1 |
| Trans-Diol % | 2.4 | 0.5 | 3.9 | 10.4 |
| Conversion % | 70.1 | 39.6 | 83.0 | 96.0 |
| Selectivity % | 4.2 | 0.5 | 7.0 | 18.7 |
| Yield % | 2.9 | 0.2 | 5.8 | 17.9 |
| Cis/Trans | 0.75 | 0 | 0.79 | 0.78 |

The invention claimed is:

1. A process for producing a 2,2,4,4-tetraalkylcyclobutane-1,3-diol of Formula II, comprising contacting a 2,2,4,4-tetraalkylcyclobutane-1,3-dione with hydrogen in the presence of a cobalt-based catalyst under conditions of temperature and pressure sufficient to form a 2,2,4,4-tetraalkylcyclobutane-1,3-diol,

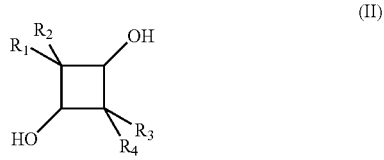

(II)

wherein each of the alkyl radicals $R_1$, $R_2$, $R_3$ and $R_4$ has, independently from each other, 1 to 8 carbon atoms; and wherein the cis/trans molar ratio of the 2,2,4,4-tetraalkyl-cyclobutane-1,3-diol is from 0.4 to 0.8; wherein the cobalt-based catalyst consists essentially of cobalt as the catalytic metal; wherein the catalyst comprises a support of silica or alumina; and wherein the selectivity is greater than about 65%.

2. The process according to claim 1, wherein each of the alkyl radical radicals $R_1$, $R_2$, $R_3$, and $R_4$ has, independently from each other, 1 to 4 carbon atoms.

3. The process according to claim 1, wherein each alkyl radical $R_1$, $R_2$, $R_3$, and $R_4$ is a methyl group.

4. The process according to claim 1, wherein a non-protic solvent comprising an unsaturated hydrocarbon, a non-cyclic ester, an ether, or a mixture thereof is present.

5. The process according to claim 4, wherein the non-cyclic ester is chosen from isopropyl isobutyrate, isobutyl propionate, octyl acetate, isobutyl isobutyrate, isobutyl acetate, and mixtures thereof.

6. The process according to claim 1, further comprising a protic solvent comprising one or more solvents chosen from a monohydric alcohol, a dihydric alcohol, a polyhydric alcohol, and mixtures thereof.

7. The process according to claim 6, wherein the protic solvent comprises methanol or ethylene glycol.

8. The process according to claim 1, wherein the cobalt-based catalyst comprises a support, and wherein the support comprises one or more of silica, alumina, or silica/alumina.

9. The process according to claim 8, wherein the support comprises a form chosen from powder, extrudate, spheres, and pellets.

10. The process according to claim 1, wherein the pressure is from 100 psi to 6000 psi.

11. The process according to claim 1, wherein the pressure is from 300 psi to 2000 psi.

12. The process according to claim 1, wherein the temperature is from 75° C. to 250° C.

13. The process according to claim 1, wherein the temperature is from 100° C. to 180° C.

14. The process according to claim 1, wherein the process is a continuous, semi-batch, or batch process.

15. A process for producing 2,2,4,4-tetramethylcyclobutane-1,3-diol, comprising contacting 2,2,4,4-tetramethylcyclobutane-1,3-dione, a cobalt-based catalyst, a non-protic solvent, and hydrogen in a hydrogenation zone under conditions of temperature and pressure sufficient to form 2,2,4,4-tetramethylcyclobutane-1,3-diol; wherein the cis/trans molar ratio of the 2,2,4,4-tetramethylcyclobutane-1,3-diol is from 0.4 to 0.8; wherein the cobalt-based catalyst consists essentially of cobalt as the catalytic metal; wherein the catalyst comprises a support of silica or alumina; and wherein the selectivity is greater than about 65%.

16. The process according to claim 15, wherein the 2,2,4,4-tetramethylcyclobutane-1,3-dione and hydrogen are continuously fed into the hydrogenation zone.

17. The process according to claim 15, wherein the hydrogenation zone has a temperature from 75° C. to 250° C.

18. The process according to claim 15, wherein the pressure is from 100 psi to 6000 psi.

19. The process according to claim 15, further comprising continuously recovering the effluent from the hydrogenation zone and recovering at least a portion of the 2,2,4,4-tetramethylcyclobutane-1,3-diol from the effluent to form a depleted 2,2,4,4-1,3-tetramethylcyclobutane-1,3-diol stream.

20. The process according to claim 19, wherein at least a portion of the depleted 2,2,4,4-1,3-tetramethylcyclobutane-1,3-diol stream is recycled to the hydrogenation zone.

21. The process according to claim 15, wherein the hydrogenation zone comprises a tubular reactor, a fixed bed reactor, a trickle bed reactor, a stirred tank reactor, a continuous stirred tank reactor, or a slurry reactor.

22. A process for producing 2,2,4,4-tetramethylcyclobutane-1,3-diol comprising:
(a) feeding isobutyric anhydride to a pyrolysis zone, wherein the isobutyric anhydride is heated at a temperature of 350° C. to 600° C. to produce a vapor effluent comprising dimethylketene, isobutyric acid, and unreacted isobutyric anhydride;
(b) cooling the vapor effluent to condense isobutyric acid and isobutyric anhydride and separating the condensate from the dimethylketene vapor;
(c) feeding the dimethylketene vapor to an absorption zone, wherein the dimethylketene vapor is contacted with a solvent comprising an ester containing 4 to 20 carbon atoms to produce an absorption zone effluent comprising a solution of dimethylketene in the solvent; wherein the ester comprises residues of an aliphatic carboxylic acid and an alkanol;
(d) feeding the absorption zone effluent to a dimerization zone wherein the absorption zone effluent is heated at a temperature of from 70° C. to 140° C. to convert dimethylketene to 2,2,4,4-tetramethylcyclobutane-1,3-dione to produce an effluent comprising a solution of 2,2,4,4-tetramethylcyclobutane-1,3-dione in the solvent; and
(e) contacting the 2,2,4,4-tetramethylcyclobutane-1,3-dione with hydrogen in the presence of a cobalt-based catalyst under conditions of temperature and pressure sufficient to form a 2,2,4,4-tetramethylcyclobutane-1,3-diol;
wherein the cis/trans molar ratio of the 2,2,4,4-tetramethylcyclobutane-1,3-diol is from 0.4 to 0.8; wherein the cobalt-based catalyst consists essentially of cobalt as the catalytic metal; wherein the catalyst comprises a support of silica or alumina; and wherein the selectivity is greater than about 65%.

* * * * *